(12) United States Patent
Burrows et al.

(10) Patent No.: US 10,618,865 B2
(45) Date of Patent: Apr. 14, 2020

(54) ORGANOMETALLIC SALT COMPOSITION, A METHOD FOR ITS PREPARATION AND A LUBRICANT ADDITIVE COMPOSITION

(71) Applicant: Ab Nanol Technologies Oy, Helsinki (FI)

(72) Inventors: Aubrey Burrows, Rickinghall (GB); Kenneth Ekman, Piispanristi (FI); Sophia Von Haartman, Åbo (FI); Samuli Lempiäinen, Åbo (FI); Johan Von Knorring, Helsinki (FI)

(73) Assignee: Ab Nanol Technologies Oy, Helsinki (FI)

( * ) Notice: Subject to any disclaimer, the term of this patent is extended or adjusted under 35 U.S.C. 154(b) by 154 days.

(21) Appl. No.: 15/740,879

(22) PCT Filed: Jun. 27, 2016

(86) PCT No.: PCT/FI2016/050463
§ 371 (c)(1),
(2) Date: Dec. 29, 2017

(87) PCT Pub. No.: WO2017/005967
PCT Pub. Date: Jan. 12, 2017

(65) Prior Publication Data
US 2018/0194707 A1 Jul. 12, 2018

(30) Foreign Application Priority Data
Jul. 7, 2015 (EP) .................................... 15175674

(51) Int. Cl.
| | | |
|---|---|---|
| *C10M 129/26* | (2006.01) | |
| *C07C 57/12* | (2006.01) | |
| *C07C 51/41* | (2006.01) | |
| *C07C 53/128* | (2006.01) | |
| *C10M 159/18* | (2006.01) | |
| *C10M 129/32* | (2006.01) | |
| *C10M 129/40* | (2006.01) | |

(52) U.S. Cl.
CPC ............ *C07C 57/12* (2013.01); *C07C 51/414* (2013.01); *C07C 53/128* (2013.01); *C10M 129/26* (2013.01); *C10M 129/32* (2013.01); *C10M 129/40* (2013.01); *C10M 159/18* (2013.01); *C10M 2203/1006* (2013.01); *C10M 2203/1025* (2013.01); *C10M 2205/0285* (2013.01); *C10M 2207/126* (2013.01); *C10N 2210/01* (2013.01); *C10N 2210/02* (2013.01); *C10N 2210/04* (2013.01); *C10N 2210/06* (2013.01); *C10N 2210/07* (2013.01); *C10N 2210/08* (2013.01); *C10N 2220/028* (2013.01); *C10N 2230/06* (2013.01); *C10N 2230/70* (2013.01)

(58) Field of Classification Search
CPC ..... C07C 57/12; C07C 53/128; C07C 51/414; C10M 159/18; C10M 129/26; C10M 129/32; C10M 129/40; C10M 2203/1006; C10M 2203/1025; C10M 2205/0285; C10M 2207/126; C10N 2210/02; C10N 2210/01; C10N 2230/70; C10N 2230/06; C10N 2220/028; C10N 2210/08; C10N 2210/07; C10N 2210/06; C10N 2210/04
See application file for complete search history.

(56) References Cited

U.S. PATENT DOCUMENTS

| | | | |
|---|---|---|---|
| 1,013,538 A | | 1/1912 | Ellis |
| 5,282,991 A | * | 2/1994 | Malcolm .............. C10M 141/00 |
| | | | 252/75 |
| 5,736,491 A | | 4/1998 | Patel et al. |
| 5,863,872 A | | 1/1999 | Garmier |
| 5,994,277 A | | 11/1999 | Ritchie et al. |
| 2012/0101013 A1 | * | 4/2012 | Mizrahi ............... C10M 125/04 |
| | | | 508/202 |

FOREIGN PATENT DOCUMENTS

| | | | |
|---|---|---|---|
| DE | 202011003324 U1 | 5/2012 | |
| EP | 0092946 A2 | 11/1983 | |
| GB | 2056482 | 3/1981 | |
| GB | 2272000 B * | 3/1997 | .......... C10M 141/06 |
| JP | H1014072 A * | 1/2003 | |
| RU | 2503713 C1 | 1/2014 | |
| WO | WO2015172846 A1 | 11/2015 | |

OTHER PUBLICATIONS

Kenbeek et al: Review of Organic Friction Modifiers—Contribution to Fuel Efficiency? SAE Technical Paper 2000-01-1792, 2000.
Ratoi et al: Mechanism of metal carboxylate friction modifier additive behaviour. International Tribology Conference, Nagasaki (JP), 2000.
Rudnick et al: Synthetic Lubricants And High-Perofrmance Functional Fluids. CRC Press, 1999.
Rudnick: Lubricant Additives. Chemistry and Applications, Second Edition, 2009.
Spikes: Boundary Lubrication and Boundary Films. Thin Films in Tribology, 1993.
Totten et al: Fuels and Lubricants Handbook: Technology Properties Performance and Testing. 2003.

* cited by examiner

*Primary Examiner* — Taiwo Oladapo
(74) *Attorney, Agent, or Firm* — Laine IP Oy

(57) ABSTRACT

The purpose of the present invention is to provide organometallic salt compositions that are useful as lubricant additives and/or in lubricant additive compositions to reduce friction and wear, and also have improved solubility in all four types of hydrocarbon base oils (Groups I-IV) at a variety of concentrations and under a variety of conditions. The organometallic salt composition is derived from at least one long chain monocarboxylic acid and a single metal in combination with at least one short or medium branched-chain monocarboxylic acid. The compositions are particularly useful in combination with activated complexes comprising a first metal component, a second metal component and particles comprising the first metal component.

16 Claims, No Drawings

ORGANOMETALLIC SALT COMPOSITION, A METHOD FOR ITS PREPARATION AND A LUBRICANT ADDITIVE COMPOSITION

RELATED APPLICATION

This application is national stage entry of PCT/FI2016/050463, filed on Jun. 27, 2016 which claims priority from European Patent Application No. 15175674, filed Jul. 7, 2015, which are incorporated by reference in their entirety.

FIELD OF THE INVENTION

The present invention relates to a novel organometallic salt composition, and a lubricant additive composition comprising the organometallic salt composition. Further, the present invention relates to a method for producing the organometallic salt composition. More particularly, the invention relates to an organometallic salt composition with a melting point below ambient temperature, allowing the use of the composition in liquid form. The organometallic composition is useful as a component in lubricant additives that reduce friction and provide wear protection, and is also soluble in a wide variety of hydrocarbon oils.

BACKGROUND OF THE INVENTION

Organometallic, salts prepared from fatty acids are frequently incorporated into oils and greases to provide lubricating compositions having special properties (see e.g. Synthetic Lubricants And High-Performance Functional Fluids, Edited by Leslie R. Rudnick and Ronald L. Shubkin, CRC Press 1999). In particular, saturated and unsaturated carboxylic acid salts are well known friction-reducing additives in lubricating oils, (Spikes, H. A. "Boundary Lubrication and Boundary Films." Proc. 19th Leeds-Lyon Symposium on Tribology, Leeds, September 1992; *Thin Films in Tribology*, ed. D Dowson et al., Elsevier 1993). The organometallic salts can be based on different metal elements as noted in the Fuels and Lubricants Handbook: Technology Properties Performance and Testing Edited by George E Totten, Steven R. Vestbrook, Rajesh Shah (2003). Copper based additives are often preferred because of their effectiveness in lubricants. Several types of copper compounds including copper dithiophosphates, dithiocarbamates, sulphonates, carboxylates, acetylacetones, phenates, copper stearate and palmitate have showed significantly lower friction and wear. Copper carboxylates, for example copper oleate, have also been used as an antioxidant, (British Pat. No. 2,056,482 and in European Pat. No. 92946 as an engine oil antioxidant). Copper-based organometallic compounds can give maximum benefit when used as multifunctional additives to reduce friction and wear in liquid lubricants or greases, fuels, cutting fluids, and hydraulic fluids. Despite all the advances in copper based lubricant additives and lubricant oil formulation technology, there remains a need for lubricant oil additives that provide even more superior wear protection and environmentally beneficial properties such as reduced exhaust emissions.

Organometallic salts useful as lubricant additives can be synthesised using a number of different reaction routes. Metal carboxylates, in particular metal salts based on long chain unsaturated or saturated fatty acids, are commonly prepared by reacting a metal carbonate with a fatty acid. One well-known method to make copper oleate is heating oleic acid with copper carbonate, (U.S. Pat. No. 1,013,538). Another process is by mixing equimolar aqueous solutions of sodium oleate and inorganic soluble salts of the desired metal, for example copper chloride. The resultant metal oleate will precipitate and it is then filtered, washed and dried; (Ratoi, M., Bovington, C. and Spikes, H. (2000) Mechanism of metal carboxylate friction modifier additive behaviour; *International Tribology Conference*, Nagasaki, JP).

The design and development of a lubricant additive to provide and impart the desired properties when added to a lubricant formulation is an unpredictable and challenging process. Moreover, the physical properties, solubility and performance of a metal carboxylate additive cannot be anticipated or determined by the chemical structure of such an organometallic compound alone. These factors do not follow simple structure-activity relationships, (Kenbeek, D., Buenemann, T., and Rieffe, H., Review of Organic Friction Modifiers—Contribution to Fuel Efficiency, SAE Technical Paper 2000-01-1792, 2000).

Most lubricant compositions include a base oil. Generally this base oil is a hydrocarbon oil or a combination of hydrocarbon oils. The hydrocarbon oils have been designated by the American Petroleum Institute as falling into Group I, II, III or IV. Of these, the Group I, II, and III oils are natural mineral oils. Group I oils are composed of fractionally distilled petroleum which is further refined with solvent extraction processes to improve properties such as oxidation resistance, and to remove wax. Group II oils are composed of fractionally distilled petroleum that has been hydrocracked to further refine and purify it. Group III oils have similar characteristics to Group II oils, with Groups II and III both being highly hydro-processed oils which have undergone various steps to improve their physical properties. Group III oils have higher viscosity indexes than Group II oils, and are prepared by either further hydrocracking of Group II oils, or by hydrocracking of hydro-isomerized slack wax, which is a byproduct of the dewaxing process used for many of the oils in general. Group IV oils are synthetic hydrocarbon oils, which are also referred to as polyalphaolefins (PAOs).

In order to modify the lubrication properties of the various base oils, additives are frequently employed. These additives include materials designed to function, for example, as antiwear agents, friction reducing additives, antioxidants, dispersants, detergents, extreme pressure additives, and corrosion inhibitors. It is highly desirable that all additives are soluble in a wide range of base oils. Good additive solubility is important to ensure that the formulated lubricant is stable with no tendency to separate or form sediments. It is also important to ensure that the additives are properly solubilized in order to enable them to function properly and perform effectively. Additive solubility is desirably maintained across a wide range of temperature and other conditions, in order to enable shipping, storage, and/or relatively prolonged use of these compositions. However, attainment of these desirable qualities should not be at the expense of overall performance. Unfortunately, some additives that provide as at least one benefit, for example friction reduction or protection against wear, also suffer from low solubility and are, therefore, of limited commercial value.

Those skilled in the art have attempted to develop alternative solutions to try and deploy additives with low solubility in lubricant formulations. One approach has been to include one or more co-base oils, such as synthetic esters or vegetable oils, in the lubricant composition. For example, esters have been used as co-base oils with polyalphaolefins for this purpose. Unfortunately, such esters often suffer from poor hydrolytic stability and thus may represent an unacceptable sacrifice in overall performance in order to achieve a remedy for the solubility problem.

Another approach to solve the problem of low solubility has been to use alternative lubricant additives containing high levels of zinc, sulphur, and/or phosphorus. These lubricant additives can offer adequate performance in terms of friction reduction and wear protection. They are, however, often less effective compared to the superior and more desirable additives based on low phosphorous, low sulphur and low sulphated ash technology.

The prior art also shows that there is a group of non-soluble lubricant additives that, depending on their structure, reduce friction and provide wear protection in a mechanical fashion by preventing direct contact between metal surfaces. Examples of additives that function in this manner are molybdenum disulphide and Teflon® fluorocarbon polymer (PTFE). These additives can be used successfully in grease compositions; however, they are not effective in lubricant oil compositions. The lubricants have been found to suffer from poor stability due to agglomeration and sedimentation of insoluble materials. As a consequence, the performance deteriorates over time and becomes unacceptable, especially in terms of friction and wear.

Yet another group of additives with low solubility consists of metal powders, for example copper alloys. These are claimed to reduce friction and wear. They are capable of forming a metal layer on the friction surfaces when deployed in lubricants. The tribo-layer is deposited on the metal surface due to physical and chemical processes. It improves the frictional conditions on the metal surfaces of moving parts and increases the loading resistance of the surfaces. These lubricant compositions, however, have been found to suffer from poor stability due to agglomeration and sedimentation of insoluble materials. As a consequence, also their performance deteriorates over time and becomes unacceptable, especially in terms of friction and wear.

A preferred group of lubricant additives that is useful in order to reduce friction and wear is that based on organometallic salts. Examples are described in Lubricant Additives: Chemistry and Applications, Second Edition, edited by Leslie R. Rudnick, CRC Press, 2009 which document is included by reference for the purpose of disclosure. It includes for example a number of copper and molybdenum compounds; specific examples are copper oleate, copper salicylate, copper naphthenate, and molybdenum naphthenate. These additives can function as very effective friction reducers and antiwear agents when used individually or preferably in combination with other compounds. The disadvantage of this group of materials is that they are most often solids at ambient temperatures and have limited oil solubility, especially when used in more saturated and paraffinic hydrocracked or synthetic base oils like Group II, III and Group IV (PAO). This limits the use of these additives in high performance automotive, industrial and off-highway lubricants.

Although the above prior art shows that useful additive compositions are available, it also demonstrates that there are significant shortcomings. There continues to be a need for high performance lubricant additive compositions that are soluble, especially when used in more saturated and paraffinic hydrocracked or synthetic base oils like Group II, III and Group IV (PAO). These important improvements are achieved in the present invention.

It has been found that copper oleate, which has a melting point of about 55° C., is significantly soluble in Group I base oils but it only has limited solubility in Group II, III, and IV base oils. This prevents copper oleate being deployed on its own or in combination with other suitable components to formulate lubricants for many applications that require Group II, III and IV higher quality base oils.

In U.S. Pat. No. 5,994,277 is disclosed a composition for improving the antioxidancy of crankcase lubricants. The composition includes three essential components, namely copper, molybdenum and one or more oil soluble aromatic amines. The copper may be added in the form of a salt of a $C_8$ to $C_{15}$ fatty acid. The molybdenum is preferably added in the form of an oil-soluble molybdenum carboxylate. The aromatic amine or mixture of aromatic amines may be an alkylated diphenylamine. An example is given where the copper is added as copper oleate and the molybdenum as molybdenum 2-ethylhexanoate.

Purpose of the Invention

The purpose of the present invention is to eliminate the drawbacks mentioned above.

A specific purpose of the present invention is to provide organometallic salt compositions that are useful as lubricant additives and/or in lubricant additive compositions to reduce friction and wear, and also have improved solubility in all four types of hydrocarbon base oils (Groups I-IV) at a variety of concentrations and under a variety of conditions.

An additional purpose of the present invention is to provide an additive composition consisting of organometallic salts in combination with other suitable components, which composition has improved solubility in all four types of hydrocarbon base oils (Groups I-IV) at a variety of concentrations and under a variety of conditions. Solubility is assessed visually, and the compositions are considered soluble if they are fully miscible with the base oil, and do not upon storage separate or form sediments or gels.

This additive composition reduces friction and fuel and/or energy consumption. Moreover, the lubricant additive composition enables increased wear protection, longer oil drain intervals and grease change intervals, reduced maintenance, and improved operational lifetime.

A further objective of the present invention is the development of high performance lubricants and greases for marine, automotive, industrial and all other off-highway applications, formulated with saturated and paraffinic hydrocracked or synthetic base oils like Group II, III and Group IV (PAO), that can ensure long-life operation of mechanical systems; protect mechanical parts from contact fatigue damages; provide high load carrying capabilities; decrease the wear of mechanical components; and provide protection for the friction surfaces from hydrogen wear and enable the self-healing of wear and damages by selective transfer. This is achieved by protecting friction surfaces with novel lubricant compositions comprising an additive composition of the present invention.

These improvements should be achieved without environmental drawbacks.

SUMMARY OF THE INVENTION

For the purpose of the present invention, a long chain carboxylic acid is $C_{13}$ to $C_{22}$.

For the purpose of the present invention, a short chain monocarboxylic acid is less than $C_6$. A short chain branched monocarboxylic acid thus has 4 or 5 carbon atoms.

For the purpose of the present invention, a medium chain monocarboxylic acid is $C_6$ to $C_{12}$.

The present invention provides, in one aspect, an organometallic salt composition derived from a single metal and at least one long chain monocarboxylic acid (also known as fatty acid), in combination with a quantity in the range 2 to 20 w-% of at least one short or medium branched-chain monocarboxylic acid, to produce an organometallic salt composition that has improved solubility in Group I, II, III or IV hydrocarbon oils. The solubility exceeds 0.1 w-%, preferably 0.5 w-% in all the hydrocarbon oil groups.

In another aspect the invention provides a method of preparing an organometallic salt composition derived from a single metal and at least one long chain monocarboxylic acid (also known as fatty acid), in combination with a quantity in the range 2 to 20 w-% of at least one short or medium branched-chain monocarboxylic acid, to produce an organometallic salt composition that has improved solubility in Group I, II, III or IV hydrocarbon oils, The solubility exceeds 0.1 w-%, preferably 0.5 w-% in all the hydrocarbon oil groups.

In yet another aspect the present invention provides a lubricant additive composition comprising an organometallic salt composition derived from a single metal and at least one long chain monocarboxylic acid combined with a quantity in the range 2 to 20 w-% of at least one short or medium branched-chain monocarboxylic acid, the lubricant additive composition being a stable liquid under ambient temperature conditions, with reduced tendency to solidify, separate, form gels, or cause sedimentation.

The lubricant additive composition described above can be formulated with other suitable components, leading to reduced friction and a reduction in the fuel and/or energy consumption as well as reduced emissions. Preferably, the lubricant additive composition according to the present invention enables the development of a lubricant that does not comprise high amounts of phosphorus or sulphur based compounds. Moreover, the lubricant additive composition enables increased wear protection, longer oil drain intervals and grease change intervals, and reduced maintenance as well as extended operational lifetime.

A particular feature of the lubricant additive composition according to the current invention is that it has been designed to provide excellent wear protection under real mechanical operating conditions. There is a problem with many prior art anti-wear agents that were developed and evaluated using standard laboratory bench, rig and engine tests. The wear rates in such tests are in the range of 1 to 10 micrometers per hour. This is done to produce a test that gives quick results. Actual wear rates in operating equipment, however, are in the range 1 to 10 nanometers per hour. This is several magnitudes lower. As a consequence, many of these standard industry tests are not representative of actual mechanical operating conditions. Also as a result, the prior art anti-wear agents do not always give effective wear protection in the field, even though they may have given very good results in standard tests.

Different and atypical wear mechanisms occur at unrealistically high wear rates in the standard tests that are not representative of actual field operating conditions. Other important antiwear mechanisms known to operate in normal conditions are prevented from occurring at high wear rates. For example, third body formation cannot take place. The third body is immediately destroyed and cannot become established. Third body formation is, however, a critical function with many new generation high performance anti-wear agents, including the current invention. Near surface intermixing may also not occur at high wear rates.

The lubrication environment at normal wear rates enables important interactions to occur between anti-wear agents and the metal surface under mixed lubrication. This has been demonstrated in work conducted at Fraunhofer Institute in Germany. The research has also confirmed the excellent wear protection provided by the current invention. The improved performance has been found to be due specifically to third body formation and also intermixing of additives into the near surface of mechanical metal parts. This demonstrates the effectiveness and superiority of the technology in the current invention compared to other prior art.

DETAILED DESCRIPTION OF THE INVENTION

The organometallic salt compositions derived from long chain monocarboxylic acids with short or medium branched-chain monocarboxylic acids useful in this invention may be characterized by way of both their generalized preparation route and certain common aspects of their structures.

The first step in the preparation of the organometallic salts in the present invention generally involves the reaction of a metal carbonate, for example copper carbonate, with at least one long chain monocarboxylic, acid, for example oleic acid. A wide range in the proportions of the carboxylic acid may be employed, such that the molar ratio of the carboxylic acid to the metal of the carbonate reactant may range from 1:1 to 20:1.

The intermediate organometallic, salts used in the invention may, more specifically, be derived from the reaction of monocarboxylic acids in the range $C_{13}$ to $C_{22}$ and the selected metal carbonate. Examples of the acids include saturated monocarboxylic, acids such as lauric, myristic, palmitic or stearic. Preferably unsaturated acids should be used such as linolenic, linoleic and oleic acids. Saturated and unsaturated branched monocarboxylic acids can also be used, for example iso-stearic acid. Optionally naphthenic acids or synthetic carboxylic acids can be used.

The metal carbonate comprises one of silver, gold, palladium, copper, cobalt, lead, tin, bismuth, molybdenum, titanium, tungsten and nickel as metal element. More preferably, the metal carbonate comprises copper or cobalt, and most preferably copper.

In a second step, the organometallic salt compositions are prepared by reacting an organometallic salt derived from one or more long chain monocarboxylic acids, for example copper oleate, with at least one short or medium branched-chain monocarboxylic acid, for example 2-ethylhexanoic acid. Initially, the carboxylic acid salt is heated to about 60° C. until it is in liquid form. The short or medium branched-chain monocarboxylic acid is added with vigorous mixing. A wide range in the proportions of the short or medium branched-chain monocarboxylic acid may be employed, such that the weight ratio of the organometallic salt and the short or medium branched-chain monocarboxylic acid may range from 2:1 to 50:1. A ratio in the range of 5:1 to 20:1 is preferred, and the range 10:1 to 20:1 is most preferred.

Saturated short or medium branched chain monocarboxylic acids are preferred in the present invention. They should contain at least one branched alkyl group and 4 to 11 carbon atoms ($C_4$ to $C_{11}$), preferably 6 to 10 carbon atoms ($C_6$ to $C_{10}$) and most preferably 8 carbon atoms ($C_8$). Examples include 2-ethylhexanoic acid, 2-methylbutyric acid, 2-ethylbutanoic acid, 2-methylpentanoic acid, 3-methylpentanoic acid, 4-methylpentanoic acid, 2-methylhexanoic acid, 5-methylhexanoic acid, 4-methyloctanoic acid, 4-methylnonanoic acid; more preferably 2-ethylbutyric acid and 2-ethylhexanoic acid; most preferably 2-ethylhexanoic acid.

Preferably, the lubricant additive is soluble in the hydrocarbon base oil both after initial mixing and for at least one week. Temperatures used for solubility testing herein include room temperature, which for the purpose of this specification is 18-24° C.

Conventional organometallic salts used as lubricant additives are typically not significantly soluble in Groups II, III or IV hydrocarbon oils. This means that the superior additives and lubricants according to the invention may be used in many applications where previously only lower performance conventional additives could be deployed.

It has been surprisingly and unexpectedly found that the organometallic salt compositions obtained by the process of the present invention, for example copper oleate reacted with 2-ethylhexanoic acid, are liquids at room temperature when the weight ratio of organometallic salt to short or medium branched chain monocarboxylic acid is in the range 5:1 to 50:1. This is especially surprising because for example, the individual compounds copper oleate and copper 2-ethylhexanoate are both solids at room temperature. The additives comprising the organometallic salt compositions according to the present invention have improved handling characteristics.

Importantly, it has been found that the organometallic salt compositions according to the current invention can be formulated with other suitable components leading to lubricant additive compositions that have improved solubility in Group I, II, III or IV hydrocarbon oils that also provide reduced friction and lower fuel and/or energy consumption as well as reduced emissions. The lubricant additive compositions according to the present invention enable the development of lubricants that do not comprise high amounts of phosphorus or sulphur based compounds. Moreover, the lubricant additive compositions enable increased wear protection, longer oil drain intervals and grease change intervals, and reduced maintenance as well as extended operational lifetime.

The organometallic salt composition according to the current invention can be combined with an activated complex containing a first metal component and a second metal component. Particles, preferably nanoparticles, are formed to provide a lubricant additive composition, and the particles include the first metal component in metallic form. The second metal component is able to reduce the metal element in the first metal component. The second metal component should be able to influence the redox potential of the metal element in the first metal component. The activated complex should contain a component that functions as a ligand. The ligand can be either a surfactant or a dispersant; examples are succinimide, poylethoxylated tallow amide and diethanol amine. The activated complex should comprise particles including the first metal component and optionally the second metal component. The activated complex should contain at least one compound improving the solubility of an oxidized form of the metal element in the first metal component, e.g. epoxy resin of diethylene glycol or epoxidized dipropylene glycol.

In addition, the activated complex also comprises at least one reducing agent, e.g. diphenyl amine or hexadecyl amine. Preferably, the difference of the standard electrode potentials of the metal element in the second metal component and the metal element in the first metal component is at least 0.2 V, based on the metallic form of each metal element and the first stable oxidized stage. Preferably, the first metal component comprises gold, silver, copper, palladium, tin, cobalt, zinc, bismuth, manganese and/or molybdenum, especially preferably copper and/or cobalt, more preferably copper. Preferably, the second metal component comprises tin, bismuth, zinc, and/or molybdenum, especially preferably, tin, bismuth and/or zinc, more preferably tin. Also preferably, the particles including a second metal component comprises the first metal component in metallic form.

The particles comprising the first and optionally the second metal component exhibit a diameter in the range of 1 to 10 000 nm, preferably in the range of 5 to 1000 nm, more preferably in the range of 10 to 500 nm, especially preferably in the range of 15 to 400 nm.

Preferably, the lubricant additive composition described above comprises a soluble metal compound derived from the first metal component. Preferably, this lubricant additive composition is able to form metal plating. This lubricant additive composition has a solubility in Group I, II, III or IV hydrocarbon oils exceeding 0.1 w-%, preferably 0.5 w-%, in all the hydrocarbon oil groups.

In the production of the activated complex, one or more alcohols are advantageously used as a reductant, solvent and/or cosolvent. Preferably, an alcohol comprising ether groups can be used, such as glycols alkylated with alkyl groups having 1 to 20 carbon atoms, e.g. diethylene glycol. Further, an alcohol having 1 to 20 carbon atoms, preferably 4 to 12 carbon atoms, such as octanol, is advantageously present.

Preferably, the weight ratio of the organometallic salt composition to the activated complex is in the range of 10000:1 to 1:1.

The preparation of the relevant activated complexes and their combination with organometallic salt compositions according to the present invention is illustrated further in example 12 below.

Processes for obtaining the activated complex referred to above are disclosed in further detail in international patent application No. PCT/EP2015/060811, hereby incorporated by reference.

EXAMPLES

Example 1: Preparation of a Modified Organometallic Salt According to the Present Invention The modified organometallic salt of the present invention can be prepared by reacting a metal salt, preferably a metal carbonate where the metal is copper, with a fatty acid, preferably oleic acid, so that the metal content of the metal carboxylate provides a metal concentration in the final salt in the range of 8-9 w-%, after which a branched short- or medium-chained monocarboxylic acid is added to the metal carboxylate. The copper carbonate and the oleic acid are reacted in an oxygen-free environment for 16 h at 150° C. After the reaction, 2-ethylhexanoic acid is added to the copper oleate at a ratio of 7.5% of the total mass of the mixture. This will result in a copper-based organometallic salt composition that is liquid at room temperature and has a melting point of 10° C., whereas a copper oleate with a metal content in the range of 8-9% not containing the branched short- or medium-chain monocarboxylic acid has a melting point of 55° C. The melting temperature was determined visually. The metal content was verified by analysis with MP-AES.

Example 2: How Melting Point is Affected by the Amount of Added Short-Chain Branched Organic Acid A modified organometallic salt was prepared according to the present invention by adding 2-ethylhexanoic acid at an amount of 11.25% of the total mass of the modified organometallic salt to copper oleate with a metal content in the range of 8-9%. The addition of 11.25% of 2-ethylhexanoic acid lowered the melting temperature of the modified organometallic salt to 4° C., whereas a modified organometallic salt of example 1 containing 7.5% 2-ethylhexanoic acid has a melting point of 10° C., and an organometallic salt consisting of only copper oleate has a melting point of 55° C. The melting temperature was determined visually.

Example 3: How Melting Point is Affected by the Amount of Added Short-Chain Branched Organic Acid A modified organometallic salt was prepared according to the present invention by adding 2-ethylhexanoic acid at an amount of 15% of the total mass of the modified organometallic salt to copper oleate with a metal content in the range of 8-9%. The addition of 15% of 2-ethylhexanoic acid lowered the melting temperature of the modified organometallic salt to below 0° C., whereas a modified organometallic salt of example 2 containing 11.25% 2-ethylhexanoic acid has a melting point of 4° C., a modified organometallic salt of example 1 containing 7.5% 2-ethylhexanoic acid has a melting point of 10° C., and an organometallic salt consisting of only copper oleate has a melting point of 55° C. The melting temperature was determined visually.

Example 4: How Melting Point is Affected by Metal Content of the Metal Carboxylate and the Amount of Branched Short- or Medium-Chain Monocarboxylic Acid To determine how the metal content and the content of branched short- or medium-chain monocarboxylic acid affect the melting temperatures of the modified organometallic salts, modified organometallic salts according to the present invention containing copper oleate with metal content in the range of 2-9% and 2-ethylhexanoic acid in the range of 1-10% were prepared. The melting temperatures were determined visually and are listed in Table 1. The metal content was verified by analysis with MP-AES.

Example 5: Preparation of Other Organometallic Salts According to the Present Invention Metal carboxylates were prepared by reacting metal carbonates with oleic acid under vacuum at 150° C. for 16 h. The metal carbonates used were bismuth subcarbonate and cobalt carbonate. The metal content by weight of the metal oleates were 5-10%. 2-ethylhexanoic acid was added at 5%, 10% and 15% of total mass of the organometallic salt until the melting temperature of the organometallic salt reached 0° C. or below 0° C. The melting temperatures are listed in Table 2.

TABLE 2

Melting temperatures of bismuth and cobalt-based organometallic salt compositions.

| Metal carboxylate | 0% 2-EHA | 5% 2-EHA | 10% 2-EHA | 15% 2-EHA |
| --- | --- | --- | --- | --- |
| Bismuth oleate (5% Bi) | 3° C. | <0° C. | — | — |
| Cobalt oleate (10% Co) | 65° C. | 35° C. | 15° C. | <0° C. |

Example 6: Solubility of the Organometallic Salt Composition of the Present Invention in a Group II Base Oil Copper based modified organometallic salts of the present invention as prepared in examples 1, 2 and 3 were blended into a Group II base oil at concentrations in the range of 0.3-3.0%. Solubility was determined visually by following the samples for 14 weeks. The results are presented in Table 3. The modified organometallic salts were regarded as soluble if no phase separation or opacity of the sample was observed.

TABLE 1

Melting temperatures of copper-based modified organic salts with metal content in the range of 2-9% with an addition of 2-ethylhexanoic acid in the range of 1-10%

| % Cu | 0% 2-EHA | 1% 2-EHA | 2% 2-EHA | 3% 2-EHA | 4% 2-EHA | 5% 2-EHA | 6% 2-EHA | 7% 2-EHA | 8% 2-EHA | 9% 2-EHA | 10% 2-EHA |
| --- | --- | --- | --- | --- | --- | --- | --- | --- | --- | --- | --- |
| 2.2% | 16° C. | 2° C. | <0° C. | <0° C. | <0° C. | <0° C. | <0° C. | <0° C. | <0° C. | <0° C. | <0° C. |
| 4.4% | 35° C. | 21° C. | 13° C. | 6° C. | 5° C. | 3° C. | 2° C. | <0° C. | <0° C. | <0° C. | <0° C. |
| 6.2% | 40° C. | >room temp | >room temp | >room temp | >room temp | 14° C. | 7° C. | 4° C. | 2° C. | <0° C. | <0° C. |
| 8.6% | 50° C. | >room temp | >room temp | >room temp | >room temp | >room temp | >room temp | 10° C. | 8° C. | 5° C. | 2° C. |

TABLE 3

Solubility in a Group II base oil.

| Organometallic salt of the present invention | 0% 2-EHA reference | 7.5% 2-EHA | 11.25% 2-EHA | 15% 2-EHA |
|---|---|---|---|---|
| 0.3% | slightly insoluble | soluble | soluble | soluble |
| 0.5% | phase separation | soluble | soluble | soluble |
| 1% | phase separation | soluble | soluble | soluble |
| 1.5% | phase separation | slightly insoluble | slightly insoluble | slightly insoluble |
| 2% | phase separation | phase separation | phase separation | phase separation |
| 2.5% | phase separation | phase separation | phase separation | phase separation |
| 3% | phase separation | phase separation | phase separation | phase separation |

The solubility of copper oleate in a Group II base oil is below 0.3%. According to the present invention, the addition of 2-ethylhexanoic acid to copper oleate results in an organometallic salt composition with improved solubility in the said base stock.

Example 7: Solubility of the Present Invention in Group III Base Oils

Copper based modified organometallic salts of the present invention as prepared in examples 1, 2 and 3 were blended into a Group III base oil at concentrations in the range of 0.3%-3%. Solubility was determined visually by following the samples for 12 weeks. The results are presented in Table 4. The modified organometallic salts were regarded as soluble if no phase separation or opacity of the sample was observed.

TABLE 4

Solubility in a Group III base oil.

| Organometallic salt of the present invention | 0% 2-EHA | 7.5% 2-EHA | 11.25% 2-EHA | 15% 2-EHA |
|---|---|---|---|---|
| 0.3% | phase separation | soluble | soluble | soluble |
| 0.5% | phase separation | soluble | soluble | soluble |
| 1% | phase separation | soluble | soluble | soluble |
| 1.5% | phase separation | soluble | soluble | soluble |
| 2% | phase separation | soluble | soluble | soluble |
| 2.5% | phase separation | slightly insoluble | soluble | soluble |
| 3% | phase separation | slightly insoluble | soluble | soluble |

Copper oleate is insoluble in a Group III base oil. According to the present invention the addition of 2-ethylhexanoic acid to copper oleate results in a modified organometallic salt with improved solubility in the said base stock.

Example 8: Solubility of the Present Invention in a Group IV Base Oil

Copper based modified organometallic salts of the present invention as prepared in example 1, 2 and 3 were blended into a Group II base oil at concentrations in the range of 0.3-3.0%. Solubility was determined visually by following the samples for 14 weeks. The results are presented in Table 4. The modified organometallic salts were regarded as soluble if no phase separation or opacity of the sample was observed.

TABLE 5

Solubility in a Group IV base oil (PAO).

| Organometallic salt of the present invention | 0% 2-EHA reference | 7.5% 2-EHA | 11.25% 2-EHA | 15% 2-EHA |
|---|---|---|---|---|
| 0.3% | clear phase separation | soluble | soluble | soluble |
| 0.5% | clear phase separation | soluble | soluble | soluble |
| 1% | clear phase separation | slightly insoluble | slightly insoluble | slightly insoluble |
| 1.5% | clear phase separation | phase separation | phase separation | phase separation |
| 2% | clear phase separation | clear phase separation | clear phase separation | clear phase separation |
| 2.5% | clear phase separation | clear phase separation | clear phase separation | clear phase separation |
| 3% | clear phase separation | clear phase separation | clear phase separation | clear phase separation |

Copper oleate is insoluble in a Group IV base oil. According to the present invention the addition of 2-ethylhexanoic acid to copper oleate results in a modified organometallic salt with improved solubility in the said base stock.

Example 9: Preparation of an Organometallic Salt Composition by Adding a Branched Long-Chain Monocarboxylic Acid to Copper Oleate To investigate the possibility of obtaining a modified organometallic salt containing a branched long-chain monocarboxylic acid with a melting temperature below ambient temperature, modified organometallic salts were prepared by adding iso-stearic acid at an amount of 1-7%, 10% and 15% of the total mass of the modified organometallic salt to copper oleate with a metal content in the range of 8-9%. The iso-stearic acid was added to copper oleate heated to 60° C. under vigorous mixing. The samples were stirred for 15 minutes to ensure homogeneity. The samples solidified as the temperature of the samples reached ambient temperature.

Example 10: Tribological Effects of the Organometallic Salt Composition

The tribological effects of the organometallic salt composition was demonstrated in tribology tests on a ball-on-three-plates system. An organometallic salt composition of the present invention was prepared by mixing copper oleate with 8 w-% 2-ethylhexanoic acid under vigorous mixing at 60-70° C. The composition was added to Chevron Taro 30

DP 40 in concentrations of 0.3%, 1% and 3% and heated to 60-70° C. under stirring for 15 min. The homogeneous oil mixtures were allowed to cool at ambient conditions. The samples were tested by tribology measurements using an Anton Paar rotational rheometer.

The measurement starts with a running-in phase to ensure flattening of the sample and constant measuring conditions. This is done at 1200 rpm for 30 minutes. After running-in the friction behavior is measured in the "Striebeck phase" during the next 10 minutes. The measuring regime starts at 0 rpm and the speed increases during the 10 minutes to 3000 rpm. The normal force is 6 N and the temperature 100° C. throughout the measurement. Wear is measured by analyzing the wear scars on the plates with optical microscope and imaging software after friction analysis.

In Examples 11 and 12, the following parameters for friction and wear tests are used:

| | |
|---|---|
| Normal force $F_N$ | 6 N |
| Temperature | 100° C. |
| Running-in phase | 1200 rpm, 30 min |
| Striebeck phase | 0-3000 rpm, 10 min |

The results of this testing are given in Table 5 and 6.

TABLE 6

Friction behavior of the samples.

| Sample description | Weight ratio | COF at 0.0001 m/s | COF at 0.001 m/s | COF at 0.01 m/s | COF at 0.1 m/s | COF at 1 m/s |
|---|---|---|---|---|---|---|
| Reference oil/no additive | 100/0 | 0.121 | 0.121 | 0.0976 | 0.109 | 0.0987 |
| Oil/organometallic salt composition | 99.7/0.3 | 0.0578 | 0.0767 | 0.0846 | 0.1035 | 0.0780 |
| Oil/organometallic salt composition | 99/1 | 0.0538 | 0.0642 | 0.0782 | 0.0983 | 0.088 |
| Oil/organometallic salt composition | 97/3 | 0.0506 | 0.0588 | 0.0694 | 0.0886 | 0.0591 |

TABLE 7

Wear behavior of the samples.

| Sample description | Weight ratio | Wear rate [nm/h] |
|---|---|---|
| Reference oil/no additive | 100/0 | 4192 |
| Oil/organometallic salt composition | 99.7/0.3 | 2442 |
| Oil/organometallic salt composition | 99/1 | 2176 |
| Oil/organometallic salt composition | 97/3 | 3589 |

From the tribology measurements it became apparent that the composition of the present invention has an advantageous impact on the friction and wear behavior.

Example 11: Tribological Effects of the Lubricant Additive Composition

An activated complex was added to a reducible adduct in order to demonstrate the tribological effects of the lubricant additive composition in tribology tests on a ball-on-three-plates system. A composition of the present invention was prepared by adding an activated complex as described in international patent application PCT/EP2015/060811 to the organometallic salt composition as prepared in Example 9 at a ratio of 2.35 w-% under vigorous mixing at 60-70° C. The composition of the present invention was added to Chevron Taro 30 DP 40 at concentrations of 0.3%, 1% and 3% and heated to 60-70° C. under stirring for 15 min. The homogeneous oil mixtures were allowed to cool at ambient conditions. The samples were tested by tribology measurements using an Anton Paar rotational rheometer according to the conditions described in example 9. The results are given in Table 7 and 8.

TABLE 8

Friction behavior of the samples.

| Sample description | Weight ratio | COF at 0.0001 m/s | COF at 0.001 m/s | COF at 0.01 m/s | COF at 0.1 m/s | COF at 1 m/s |
|---|---|---|---|---|---|---|
| Reference oil/no additive | 100/0 | 0.121 | 0.121 | 0.0976 | 0.109 | 0.0987 |
| Oil/additive composition | 99.7/0.3 | 0.0706 | 0.0692 | 0.07745 | 0.0955 | 0.0755 |
| Oil/additive composition | 99/1 | 0.06875 | 0.06475 | 0.07435 | 0.0928 | 0.0755 |
| Oil/additive composition | 97/3 | 0.0539 | 0.05545 | 0.06805 | 0.0876 | 0.0825 |

TABLE 9

Wear behavior of the samples.

| Sample description | Weight ratio | Wear rate [nm/h] |
|---|---|---|
| Reference oil/no additive | 100/0 | 4192 |
| Oil/additive composition | 99.7/0.3 | 3059 |
| Oil/additive composition | 99/1 | 1924 |
| Oil/additive composition | 97/3 | 1870 |

From the tribology measurements it became apparent that the composition of the present invention has an advantageous impact on the friction and wear behavior.

Example 12: Preparation of Combinations of an Activated Complex and an Organometallic Salt Composition According to the Invention a) Organometallic Salt Composition Based on Copper The preparation of the activated complex involves a three-step process.

The first step is preparation of copper (II) chloride solution. Diethylene glycol (about 3.5 kg) was placed in a glass-lined vessel fitted with a stirrer and heating capability. This was heated to about 40° C. and copper chloride (0.357 kg) was slowly added with stirring to ensure the material is totally dissolved. C-5A succinimide (2.1 kg) was then slowly added with stirring but no heating. Diphenylamine (1.72 kg) was next added in small portions and the mixture was stirred to ensure it was homogenous. Finally DEG-1 epoxy resin (1.86 kg) was added and thoroughly stirred.

The second step is preparation of tin (IV) chloride solution. In a separate glass-lined vessel fitted with a stirrer and heating capability, Tin (IV) chloride pentahydrate (4.2 kg) was dissolved in octanol (about 9.8 kg) by stirring the mixture at about 40° C.

The third step is making of the activated complex. In a separate glass-lined vessel fitted with a stirrer and cooling capability, the tin (IV) chloride solution prepared above was added to the copper (II) chloride solution also prepared above under stirring. The tin (IV) chloride solution was added in small portions and the temperature must be maintained below 50° C. After the addition was complete the mixture was stirred for a further period to ensure it was homogenous.

The activated complex (3 grams) is added to a solution of copper-based organometallic salt composition (125 grams) prepared according to Example 1 in a glass-lined vessel fitted with a stirrer and heating capability. The temperature of the mixture was maintained at about 60° C. and stirred for a further period to ensure it was homogenous.

b) Organometallic Salt Composition Based on Cobalt

A modified organometallic salt according to the present invention is prepared by reacting cobalt carbonate with oleic acid, so that the metal content of the metal carboxylate provides a metal concentration in the final salt in the range of 8-9 w-%, after which 2-ethylhexanoic acid is added to the metal carboxylate. Cobalt carbonate hexahydrate and oleic acid are reacted in an oxygen-free environment for 16 h at 150° C. After the reaction, 2-ethylhexanoic acid is added to the cobalt oleate at a ratio of 10% of the total mass of the mixture. This will result in a cobalt-based organometallic salt composition that is liquid at room temperature and has a melting point of 15° C. The melting point was determined visually. The metal content was verified by analysis with MP-AES.

Preparation of the activated complex is carried out as described above.

The activated complex (3 grams) made above is added to the cobalt-based organometallic salt composition (125 grams) in a glass-lined vessel fitted with a stirrer and heating capability. The temperature of the mixture was maintained at about 60° C. and stirred for a further period to ensure it was homogenous.

The invention claimed is:

1. An organometallic salt composition comprising:
an organometallic salt of a single metal and at least one $C_{13}$ to $C_{22}$ monocarboxylic acid, and
at least one $C_4$-$C_{12}$ branched-chain monocarboxylic acid, wherein said organometallic salt composition has a solubility exceeding 0.1 w-%, in each of hydrocarbon oil Groups I, II, III and IV, and wherein a weight ratio of the organometallic salt to the at least one $C_4$-$C_{12}$ branched chain monocarboxylic acid is from 5:1 to 50:1.

2. The organometallic salt composition according to claim 1 having a solubility in the Group I, II, III and IV hydrocarbon oils exceeding 0.5 w-%.

3. The organometallic salt composition according to claim 1, wherein the at least one branched-chain of the at least one $C_4$-$C_{12}$ branched-chain monocarboxylic acid contains at least one branched alkyl group that is methyl or ethyl.

4. The organometallic salt composition according to claim 3, wherein the at least one $C_4$-$C_{12}$ branched-chain chain monocarboxylic acid is 2-ethylhexanoic acid.

5. The organometallic salt composition according to claim 1, wherein the at least one $C_{13}$ to $C_{22}$ monocarboxylic acid is oleic acid.

6. The organometallic salt composition according to claim 1, wherein the metal salt comprises copper oleate.

7. The organometallic salt composition according to claim 1, wherein the organometallic salt is soluble in each of hydrocarbon oil Groups I, II, III and IV for at least one week at a temperature in the range 18 to 24° C.

8. The organometallic salt composition according to claim 1, wherein the organometallic salt is soluble in Group II, III and IV base oils at a ratio of hydrocarbon oil to organometallic salt composition ranging from 100:1 to 200:1.

9. A method for preparing an organometallic salt composition comprising:
reacting at least one $C_{13}$ to $C_{22}$ monocarboxylic acid with a metal carbonate selected from the group consisting of silver, gold, palladium, copper, cobalt, lead, tin, bismuth, molybdenum, titanium, tungsten and nickel carbonate to form the organometallic salt, and
mixing at least one $C_4$-$C_{12}$ branched-chain monocarboxylic acid with the formed organometallic salt to lower a melting point of the organometallic salt and form the organometallic salt composition, wherein a weight ratio of the organometallic salt to the at least one $C_4$-$C_{12}$ branched chain monocarboxylic acid is from 5:1 to 50:1.

10. The method according to claim 9, wherein the metal carbonate comprises copper or cobalt carbonate.

11. The method according to claim 9, wherein a molar ratio of the at least one $C_{13}$ to $C_{22}$-monocarboxylic acid to the metal of the metal carbonate is in a range of 1:1 to 20:1.

12. The method according to claim 9, wherein the organometallic salt is heated to about 60° C. and the at least one $C_4$-$C_{12}$ branched-chain monocarboxylic acid is then added via the mixing.

13. A lubricant composition comprising a hydrocarbon oil of Group I, II, III, or IV and the organometallic salt composition of claim 1 solubilized therein.

14. The lubricant composition according to claim 13, further comprising an activated complex containing:
a first metal component and a second metal component, and
particles comprising the first metal component and optionally the second metal component.

15. The lubricant composition according to claim 13, wherein the organometallic salt composition comprises a solubility in the Group I, II, III or IV hydrocarbon oil exceeding 0.1 w-%.

16. The organometallic salt composition according to claim 1, wherein the at least one $C_4$-$C_{12}$ branched-chain monocarboxylic acid comprises 2 to 20 w-% of a total weight of the salt composition.

* * * * *